US009840232B1

(12) United States Patent
Low et al.

(10) Patent No.: US 9,840,232 B1
(45) Date of Patent: Dec. 12, 2017

(54) DUAL MODE OPTICAL RAIN SENSING DEVICE

(71) Applicant: Delphi Technologies, Inc., Troy, MI (US)

(72) Inventors: Yew Kwang Low, Singapore (SG); Kok Wee Yeo, Singapore (SG); Ke Tan, Singapore (SG)

(73) Assignee: DELPHI TECHNOLOGIES, INC., Troy, MI (US)

( * ) Notice: Subject to any disclaimer, the term of this patent is extended or adjusted under 35 U.S.C. 154(b) by 0 days.

(21) Appl. No.: 15/237,746

(22) Filed: Aug. 16, 2016

(51) Int. Cl.
*B60S 1/08* (2006.01)
*G01N 21/55* (2014.01)
*G01N 21/552* (2014.01)
*G01N 21/47* (2006.01)

(52) U.S. Cl.
CPC .......... *B60S 1/0837* (2013.01); *G01N 21/552* (2013.01); *G01N 2021/4735* (2013.01)

(58) Field of Classification Search
CPC ................ B60S 1/0837; G01N 21/552; G01N 2021/4735
See application file for complete search history.

(56) References Cited

U.S. PATENT DOCUMENTS

| 5,483,346 A | * | 1/1996 | Butzer | G01J 4/00 250/225 |
| 2011/0031921 A1 | * | 2/2011 | Han | B60S 1/0837 318/483 |

* cited by examiner

*Primary Examiner* — Rodney Butler
(74) *Attorney, Agent, or Firm* — Lawrence D. Hazelton

(57) ABSTRACT

An illustrative example embodiment of a device for detecting rain or a substance on a windshield includes at least one radiation source, an internal reflection sensor situated to detect at least some of a first portion of the radiation that reflects from the windshield. The internal reflection sensor provides a first output that has a characteristic that differs based on whether at least one raindrop is on the windshield. A scattered reflection sensor is situated to detect at least some of a second portion of the radiation reflecting from rain near the windshield or a substance on the windshield. The scattered reflection sensor provides a second output indicative of an amount of radiation incident on the scattered reflection sensor. A processor is configured to determine a condition of the windshield based on the first output and the second output.

20 Claims, 3 Drawing Sheets

DUAL MODE OPTICAL RAIN SENSING DEVICE

BACKGROUND

Modern day vehicles include a variety of electronic components that increase driver safety and convenience. Rain sensors for automatically activating windshield wipers are one such component. Many rain sensors are optical devices that utilize internal reflection of light from a windshield. Raindrops on a windshield change the amount of reflected light and such information is used for automatically controlling the windshield wipers.

One drawback associated with current rain sensors is that they require prisms and collimating lenses to guide light at an appropriate angle to realize the total internal reflection conditions required for such devices to operate as designed. Lenses, prisms and optical coupling elements require additional space and increase the number of components and expense of such devices.

Another drawback associated with known rain sensing devices is that they are typically not capable of detecting a continuous water film or a coating on a windshield. The way in which the internal reflection arrangements of known sensors operate typically depends upon individual raindrops contacting the windshield and a broader coating of water may not be detectable.

It would be useful to provide a rain sensor for use in connection with a vehicle windshield wiper system that is lower cost, requires less space and provides more robust rain sensing.

SUMMARY

An illustrative example embodiment of a device for detecting rain or a substance on a windshield includes at least one radiation source that emits radiation toward a detection area on the windshield in a direction such that a first portion of the radiation reflects from the windshield and a second portion of the radiation passes through the windshield. An internal reflection sensor is situated relative to the radiation source such that at least some of the first portion of the radiation that reflects from the detection area on the windshield is incident on the internal reflection sensor. The internal reflection sensor provides a first output that is indicative of an amount of the first portion of the radiation that is incident on the internal reflection sensor. The first output has a characteristic that differs based on whether at least one raindrop is on the windshield in the detection area. A scattered reflection sensor is situated relative to the radiation source differently than the internal reflection sensor such that at least some of the second portion of the radiation reflecting from rain near the windshield or a substance on the windshield may be incident on the scattered reflection sensor. The scattered reflection sensor provides a second output indicative of an amount of radiation incident on the scattered reflection sensor. A processor is configured to determine a condition of the windshield based on the first output and the second output.

In an example embodiment having one or more features of the device of the previous paragraph, the radiation source emits light.

In an example embodiment having one or more features of the device of either of the previous paragraphs, the radiation source comprises a laser diode.

In an example embodiment having one or more features of the device of any of the previous paragraphs, the radiation source comprises a near infrared laser diode.

In an example embodiment having one or more features of the device of any of the previous paragraphs, the characteristic of the first output includes a first magnitude and a first frequency.

In an example embodiment having one or more features of the device of any of the previous paragraphs, the processor is configured to determine if the first magnitude exceeds at least one predetermined magnitude threshold and to determine if the first frequency exceeds at least one frequency threshold.

In an example embodiment having one or more features of the device of any of the previous paragraphs, the processor is configured to: determine that the condition of the windshield is a first condition that includes a first level of precipitation when the first magnitude exceeds a first magnitude threshold and the second output does not indicate any radiation incident on the scattered reflection sensor; determine that the condition of the windshield is a second condition that includes a second level of precipitation that is greater than the first level of precipitation when the first magnitude exceeds a second magnitude threshold that is higher than the first magnitude threshold and the second output indicates radiation incident on the scattered reflection sensor; and determine that the condition of the windshield is a third condition that includes a third level of precipitation that is greater than the second level of precipitation when the first magnitude exceeds a third magnitude threshold that is greater than the second magnitude threshold and the second output indicates radiation incident on the scattered reflection sensor with a high frequency of incidence.

In an example embodiment having one or more features of the device of any of the previous paragraphs, the processor is configured to: control a windshield wiper assembly based on the determined condition of the windshield; cause the windshield wiper assembly to swipe the windshield once based on determining that the condition of the windshield is the first condition; cause the windshield wiper assembly to operate at one of a low, medium or high speed based on the first frequency and a frequency of incidence of radiation incident on the scattered reflection sensor when the condition of the windshield is the second condition; and cause the windshield wiper assembly to operate at a high speed when the condition of the windshield is the third condition.

In an example embodiment having one or more features of the device of any of the previous paragraphs, the processor is configured to determine that a substance is on the windshield when the first output does not indicate any rain on the detection area and the second output indicates that radiation is incident on the scattered reflection sensor at a high frequency of incidence, and cause a windshield wiper assembly to apply a windshield cleaner fluid to the windshield.

An example embodiment having one or more features of the device of any of the previous paragraphs includes at least one transreflective component between the radiation source and the windshield. The transreflective component allows the first portion of the radiation to pass through the transreflective component toward the detection area on the windshield and reflects a third portion of the radiation toward a second detection area on the windshield. A second internal reflection sensor is situated relative to the radiation source such that at least some of the third portion of the radiation that reflects from the second detection area on the windshield is incident on the second internal reflection sensor.

The second internal reflection sensor provides a third output that is indicative of an amount of the third portion of the radiation that is incident on the second internal reflection sensor. The third output has a characteristic that differs based on whether at least one raindrop is on the windshield in the second detection area.

In an example embodiment having one or more features of the device of any of the previous paragraphs, the first portion of the radiation is directed at the detection area on the windshield at an angle that results in the first portion of the radiation reflecting from the detection area toward the internal reflection sensor, and the third portion of the radiation is directed at the second detection area on the windshield at an angle that results in at least some of the third portion of the radiation reflecting from the second detection area toward the second internal reflection sensor.

In an example embodiment having one or more features of the device of any of the previous paragraphs, the first portion of the radiation is directed at the detection area on the windshield at an angle that results in the first portion of the radiation reflecting from the detection area toward the internal reflection sensor, and the characteristic of the first output includes a first magnitude that decreases in an amount corresponding to an amount of rain on the detection area.

An illustrative example embodiment of a method of detecting rain or a substance on a windshield includes: emitting radiation toward a detection area on the windshield in a direction such that a first portion of the radiation reflects from the windshield and a second portion of the radiation passes through the windshield; using an internal reflection sensor for detecting at least some of the first portion of the radiation that reflects from the detection area on the windshield that is incident on the internal reflection sensor; generating a first output from the internal reflection sensor that is indicative of an amount of the first portion of the radiation that is incident on the internal reflection sensor, the first output having a characteristic that differs based on whether at least one raindrop is on the windshield in the detection area; using a scattered reflection sensor for detecting at least some of the second portion of the radiation reflecting from rain near the windshield or a substance on the windshield; generating a second output from the scattered reflection sensor indicative of an amount of radiation incident on the scattered reflection sensor; and determining a condition of the windshield based on the first output and the second output.

In an example embodiment having one or more features of the method of the previous paragraph, the radiation comprises light.

In an example embodiment having one or more features of the method of either of the previous paragraphs, the characteristic of the first output includes a first magnitude and a first frequency.

An example embodiment having one or more features of the method of any of the previous paragraphs includes determining if the first magnitude exceeds at least one predetermined magnitude threshold, and determining if the first frequency exceeds at least one frequency threshold.

An example embodiment having one or more features of the method of any of the previous paragraphs includes: determining that the condition of the windshield is a first condition that includes a first level of precipitation when the first magnitude exceeds a first magnitude threshold and the second output does not indicate any radiation incident on the scattered reflection sensor; determining that the condition of the windshield is a second condition that includes a second level of precipitation that is greater than the first level of precipitation when the first magnitude exceeds a second magnitude threshold that is higher than the first magnitude threshold and the second output indicates radiation incident on the scattered reflection sensor; and determining that the condition of the windshield is a third condition that includes a third level of precipitation that is greater than the second level of precipitation when the first magnitude exceeds a third magnitude threshold that is greater than the second magnitude threshold and the second output indicates radiation incident on the scattered reflection sensor with a high frequency of incidence.

An example embodiment having one or more features of the method of any of the previous paragraphs includes controlling a windshield wiper assembly based on the determined condition of the windshield including: causing the windshield wiper assembly to swipe the windshield once based on determining that the condition of the windshield is the first condition; causing the windshield wiper assembly to operate at one of a low, medium or high speed based on the first frequency and a frequency of incidence of radiation incident on the scattered reflection sensor when the condition of the windshield is the second condition; and causing the windshield wiper assembly to operate at a high speed when a condition of the windshield is the third condition.

An example embodiment having one or more features of the method of any of the previous paragraphs includes determining that a substance is on the windshield when the first output does not indicate any rain on the detection area and the second output indicates that radiation is incident on the scattered reflection sensor at a high frequency of incidence, and causing a windshield wiper assembly to apply a windshield cleaner fluid to the windshield.

An example embodiment having one or more features of the method of any of the previous paragraphs includes: directing a third portion of the radiation toward a second detection area on the windshield; using a second internal reflection sensor for detecting at least some of the third portion of the radiation that reflects from the second detection area on the windshield; and generating a third output from the second internal reflection sensor that is indicative of an amount of the third portion of the radiation that is incident on the second internal reflection sensor, the third output having a characteristic that differs based on whether at least one raindrop is on the windshield in the second detection area.

The various features and advantages of at least one disclosed example embodiment will become apparent to those skilled in the art from the following detailed description. The drawings that accompany the detailed description can be briefly described as follows.

DETAILED DESCRIPTION

Figure 1:
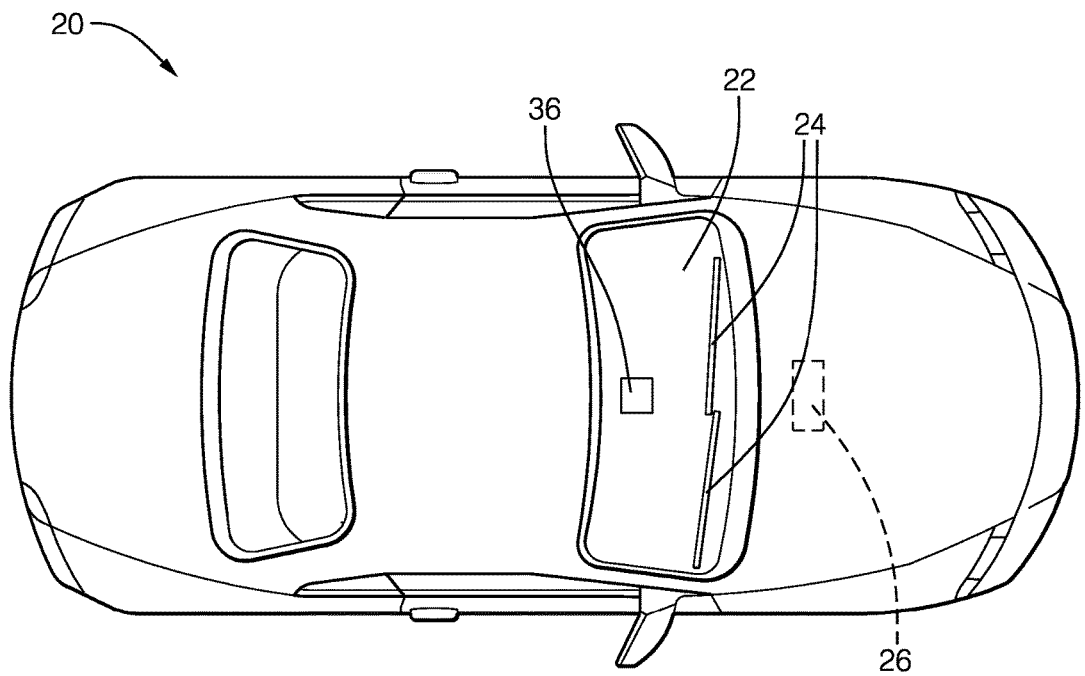
FIG. 1 schematically illustrates a vehicle including a device for detecting rain or a substance on a windshield of the vehicle designed according to an embodiment of this invention.

FIG. 1 schematically illustrates a vehicle 20 including a windshield 22. Windshield wipers 24 selectively swipe across the windshield 22. A controller 26 includes at least one processor with associated memory. The controller 26 is particularly configured for controlling operation of the windshield wipers 24. The controller 26 may be a dedicated computing device or be a portion of a computing device that performs control functions for other portions of the vehicle 20.

A device 30 for detecting rain or a substance on the windshield 22 provides information to the controller 26 for operating the windshield wipers 24. The device 30 may be situated at any location adjacent the windshield 22 and in the illustrated example, is positioned where a rearview mirror base would be secured to the windshield 22.

Figure 2:
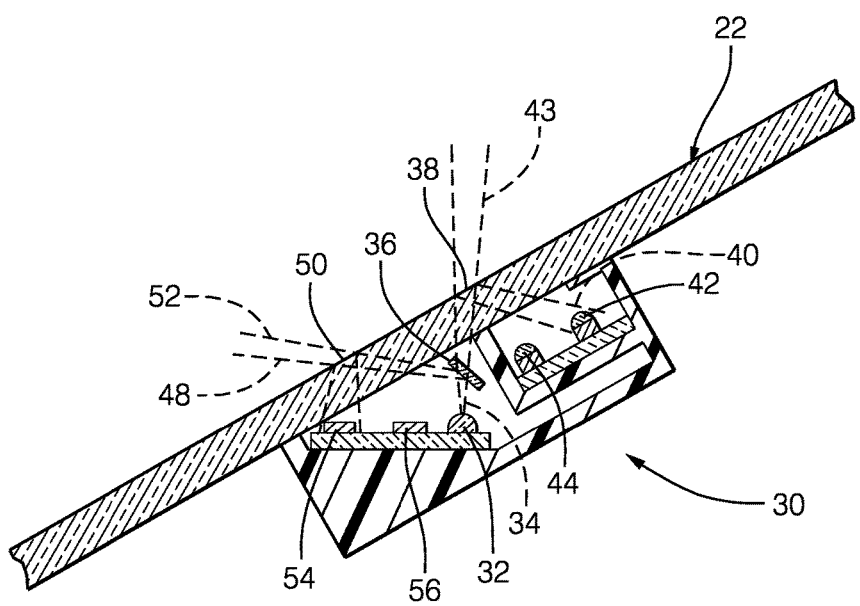
FIG. 2 schematically illustrates an example embodiment of a device for detecting rain or a substance on a windshield.

FIG. 2 schematically illustrates an example embodiment of the device 30 for detecting rain or a substance on the windshield 22. In this example, at least one source of radiation 32 emits radiation as schematically shown at 34. In the illustrated example, a transreflective component 36 is situated between the source of radiation 32 and the windshield 22. The transreflective component 36 allows a first portion of the radiation 34 to pass through the transreflective component 36 and travel toward the windshield 22. The first portion of the radiation 34 reflects from a detection area 38 on the windshield 22. Resulting reflected radiation is schematically shown at 40.

In one example, the source of radiation 32 comprises a laser diode and the radiation comprises light. In one example, the source of radiation 32 is a near infrared laser diode.

An internal reflection sensor 42 is situated relative to the source of radiation 32 and the windshield 22 such that at least some of the first portion of radiation that is reflected at 40 will be incident on the internal reflection sensor 42. The amount of radiation detected by the internal reflection sensor 42 depends upon the angle at which the radiation encounters the outer surface of the windshield 22 at the detection area 38 and whether any raindrops are in the detection area 38.

As schematically shown in FIG. 2, a second portion 43 of the radiation from the radiation source 32 passes through the windshield 22. A scattered reflection sensor 44 is situated relative to the source of radiation 32 differently than the internal reflection sensor 42. The scattered reflection sensor 44 does not normally detect any of the reflected radiation schematically shown at 40 reflecting from the detection area 38 on the windshield 22. The scattered reflection sensor 44 may detect radiation that reflects from one or more raindrops near the windshield 22 if such a raindrop encounters the second portion of the radiation schematically shown at 43.

The transreflective component 36 also directs a third portion of radiation schematically shown at 48 toward a second detection area 50 on the windshield 22 by reflecting such radiation toward the second detection area 50. At least some of the radiation reflected by the transreflective component 36 passes through the windshield as schematically shown at 52.

A second internal reflection sensor 54 is situated relative to the source of radiation 32 such that at least some of the radiation reflected from the second detection area 50 will be incident on the second internal reflection sensor 54. In this example, a second scattered reflection sensor 56 is situated relative to the source of radiation 32 where radiation reflecting from the windshield 22 is not normally incident on the scattered reflection sensor 56.

In an example embodiment, the transreflective component 36 is an optical component that facilitates directing radiation, such as light, in two directions as schematically shown in FIG. 2. In one example, the transreflective component 36 comprises a prism. In another example embodiment, the transreflective component 36 comprises a grating. In some examples, the transreflective component 36 comprises a mirror while in other embodiments, the transreflective component 36 comprises a lens. Some example embodiments include a transreflective component that has characteristics or features of a combination of two or more of a prism, a grating, a lens and a mirror.

In an example embodiment, the internal reflection sensors 42 and 54 comprise photodetectors or light sensors. The scattered reflection sensors 44 and 56 comprise photodetectors or light sensors. Some embodiments include known photodetectors such as photo-multipliers, PIN photodiodes, and avalanche photodiodes.

Figure 3:
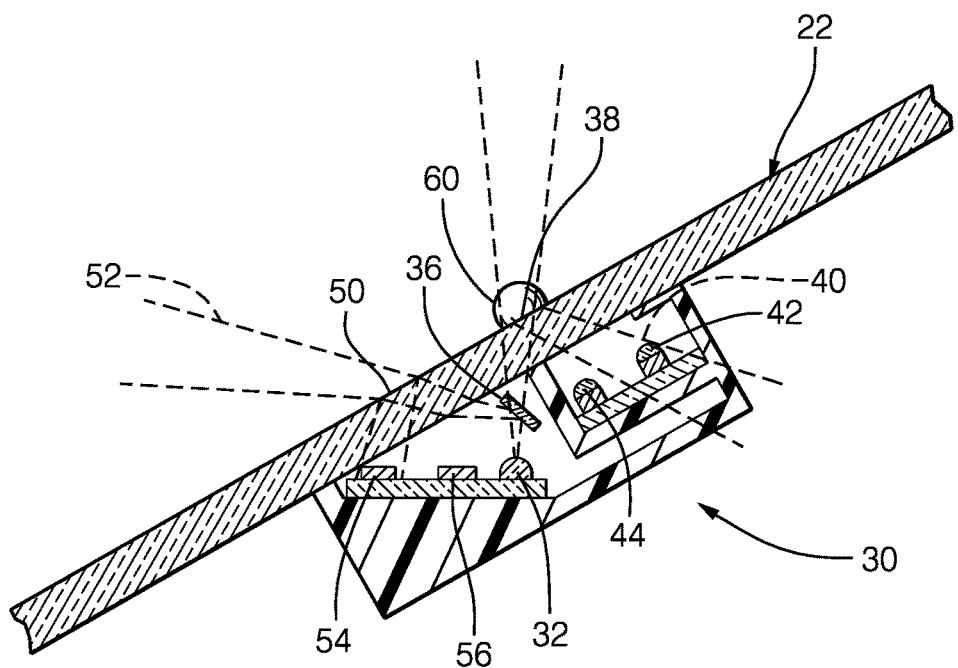
FIG. 3 illustrates selected features of an example operating condition of the embodiment of FIG. 2.

FIG. 3 schematically illustrates operation of the device 30 under a first condition of the windshield that includes at least one raindrop 60 in the detection area 38. The amount of radiation or light detected by the internal reflection sensor 42 is different when the raindrop 60 is in the detection area 38 compared to a condition where nothing is on the windshield 22. The presence of the raindrop alters the amount of radiation or light reflected from the windshield 22 toward the internal reflection sensor 42.

A first output from the internal reflection sensor 42 has a first characteristic that changes depending on the presence or absence of any raindrops in the detection area 38. For example, the first output from the internal reflection sensor 42 has a magnitude and a frequency. The magnitude in this example will decrease based on a decreased amount of reflected radiation detected by the internal reflection sensor 42 because of the presence of the raindrop 60 in the detection area 38. The frequency of the first output in this example corresponds to the number of changes in the magnitude that occur over a selected measurement period. For example, more raindrops contacting the detection area 38 will cause the change in magnitude of the first output to occur more often. The controller 26 uses information regarding the first characteristic of the first output including the magnitude and the frequency according to an example embodiment for detecting rain and controlling the windshield wipers 24 according to a determined condition of the windshield 22.

In FIG. 3, no airborne airdrops cause any reflection of any of the radiation or light that passes through the windshield 22 and neither of the scattered reflection sensors 44 or 56 provides any output regarding any raindrop detection. Also in FIG. 3 there is no rain present on the second detection area 50 such that the output from the internal reflection sensor 54 does not indicate the presence of any rain.

Figure 4:
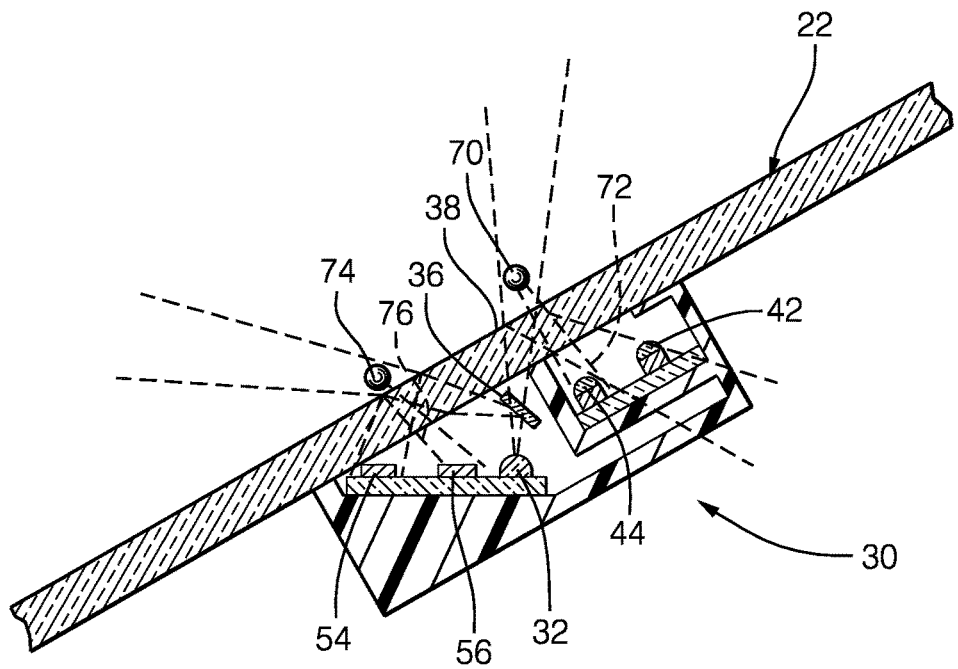
FIG. 4 schematically illustrates selected portions of another example operating condition of the example embodiment of FIG. 2.

FIG. 4 schematically illustrates a situation in which raindrops are approaching but have not yet contacted the windshield 22. A raindrop 70 encounters radiation that has passed through the windshield 22 and reflects at least some of that radiation as schematically shown at 72 toward the scattered reflection sensor 44. When this occurs, the scattered reflection sensor 44 provides a second output that indicates the incidence of radiation on that sensor. The second output may have a magnitude and a frequency indicating an amount of incident or detected radiation and a number of times that radiation is detected within a measurement period, respectively, for example. Another raindrop 74 is shown in FIG. 4 that encounters radiation passing through the windshield 22 after having been reflected by the transreflective component 36. At least some of the radiation reflects off the raindrop 74 as schematically shown at 76. The scattered reflection sensor 56 provides a second output indicating the radiation detected by that sensor.

The conditions shown in FIGS. 3 and 4 may occur simultaneously and the device 30 is capable of providing first outputs from the internal reflection sensors 42 and 54 and second outputs from the scattered reflection sensors 44 and 56 simultaneously to provide a more robust rain detection system compared to one that would only be able to detect the respective conditions shown in FIGS. 3 and 4. One feature of the illustrated example embodiment is that it is a dual mode sensing system that allows for detecting rain using internal reflections based off of radiation reflecting from the windshield toward a sensor and external scattered reflections that are based off of radiation reflecting from raindrops or another substance external to the windshield 22.

Figure 5:
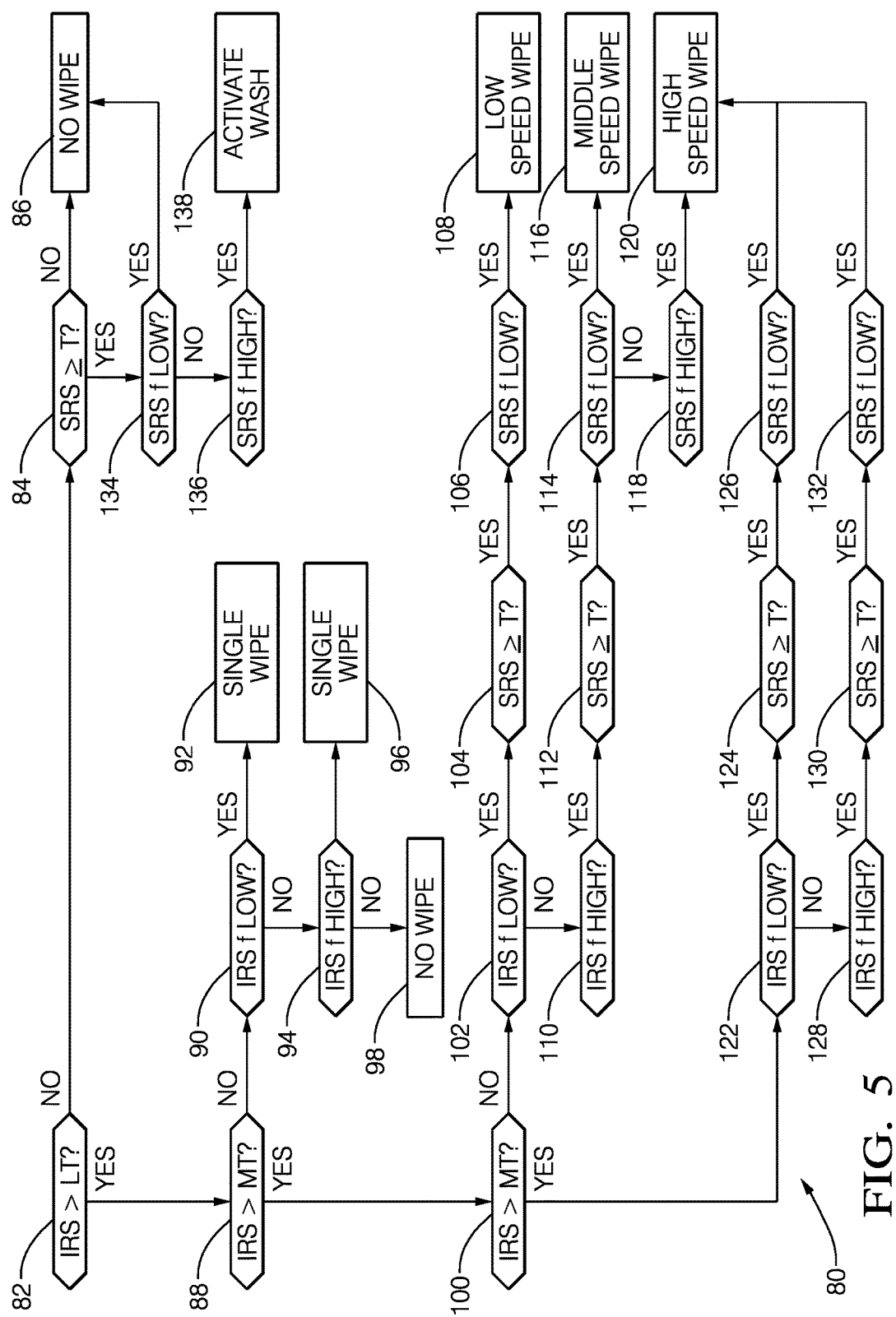
FIG. 5 is a flowchart diagram illustrating an example embodiment of a control technique based on information from a device, such as the example embodiment of FIG. 2.

FIG. 5 is a flowchart diagram 80 that summarizes an example control approach used by the controller 26 for controlling operation of the windshield wipers 24 depending on a detected condition of the windshield 22. The process summarized in FIG. 5 begins at 82 where the first output from at least one internal reflection sensor (IRS) is compared to a low threshold (LT). If the first output magnitude from at least one internal reflection sensor 42, 54 does not exceed the low threshold, which is preselected, a determination is made at 84 whether at least one scattered reflection sensor (SRS) output exceeds a threshold (T), which is preselected. If there is no output from a scattered reflection sensor 44 or 56 that exceeds the threshold, then the controller 26 determines that no wiper operation is required as shown at 86.

If the first output from an internal reflection sensor exceeds the low threshold at 82, a determination is made at 88 whether that output exceeds a middle threshold (MT). If not, then the first output from at least one internal reflection sensor indicates that there is something at a detection area causing a change in the amount of radiation detected by the internal reflection sensor having a relatively low magnitude of change. A determination is made at 90 whether a frequency of the characteristic of the first output from the internal reflection sensor is low. If so, then the controller 26 determines that the condition of the windshield 22 includes very light rain, such as precipitation at a rate that is less than 0.25 mm per hour. Under this condition, the controller 26 causes the windshield wipers 24 to operate by making a single wipe across the windshield 22 as shown at 92.

If the frequency of the first output from the internal reflection sensor is not low, a determination is made whether the frequency is high at 94. If so, the controller 26 determines that the condition of the windshield includes mist and the controller 26 causes a single wipe by the windshield wipers 24 across the windshield 22 as shown at 96.

Under some conditions, the output from the internal reflection sensor will be sufficient to exceed the low threshold (LT) but the frequency will be low enough that there is no need for any windshield wiper activation and the controller 26 determines such a condition at 98. This may occur, for example, when there are passing shadows over the windshield 22 that alter an amount of radiation detected by at least one of the internal reflection sensors 42 or 54.

If the first output from at least one of the internal reflection sensors exceeds the low threshold at 82 and the middle threshold (MT) at 88, then a determination is made at 100 whether the sensor output exceeds a high threshold (HT) at 100. If not, then the first output from at least one of the internal reflection sensors is processed by the controller 26 to determine whether the frequency of the first output is low at 102. If so, a determination is made at 104 whether there is an output from at least one scattered reflection sensor (SRS) 44 or 54 that exceeds a threshold (T). If the result of that determination is positive, then a determination is made at 106 whether the frequency of the output from the scattered reflection sensor is low. If so, then the controller 26 causes windshield wiper operation at 108 to activate the windshield wipers 24 at a low speed wipe. In this scenario, the controller 26 determines that a condition of the windshield 22 includes light rain, such as a precipitation rate between 0.25 mm per hour and 1.0 mm per hour.

If the determination made at 102 is negative, the frequency of the first output from an internal reflection sensor is not low and a determination is made at 110 whether that frequency is high. If so, an output from the scattered reflection sensors is checked at 112 to determine if at least one of them exceeds the threshold (T). Provided that there is at least some output from a scattered reflection sensor 44 or 54, a frequency of that output is checked at 114 to determine whether the frequency is low. If that determination results in a positive outcome, the controller 26 causes a middle speed wipe windshield wiper operation at 116. In this instance, the controller 26 determines that a condition of the windshield 22 includes moderate rain, such as a precipitation rate between 1.0 mm per hour and 4.0 mm per hour.

If the determination made at 114 does not indicate that the frequency of the output from the scattered reflection sensor is low, a determination is made at 118 whether such frequency is high. If so, the controller 26 causes a high speed wiper operation at 120. In this instance, the controller 26 determines that the condition of the windshield 22 includes heavy rain, such as a precipitation rate between 4.0 mm per hour and 16.0 mm per hour.

Under some conditions, the magnitude of the output from at least one of the internal reflection sensors will exceed the high threshold at 100 and, according to the example process shown in FIG. 5, a determination is then made at 122 regarding whether the frequency of the output from the internal reflection sensor is low. If so, output from the scattered reflection sensors are checked at 124. Provided that there is an output from a scattered reflection sensor that exceeds the threshold (T), a check is made whether the frequency of that output is high at 126. If the result of that determination is positive, the controller 26 causes high speed wiper operation at 120. In this instance, the controller 26 determines that the condition of the windshield 22 includes very heavy rain, such as a precipitation rate between 16.0 mm per hour and 50.0 mm per hour.

If the frequency of the output from the internal reflection sensor checked at 122 is determined not to be low, a check is made at 128 whether that frequency is high. If so, output from a scattered reflection sensor is verified at 130. If the frequency of the scattered reflection sensor output is high at 132, the controller 26 proceeds to cause high speed wiper operation at 120. In this instance, the controller 26 effectively determines that a condition of the windshield 22 includes extreme rain, such as a precipitation rate that is greater than 50.0 mm per hour.

One feature of the example embodiment of a rain or substance detector device 30 is that it is also capable of detecting when debris or another substance besides rain is present on the windshield 22. In FIG. 5, under a condition where no internal reflection sensor provides an output that exceeds the low threshold as checked at 82 and a scattered reflection sensor output exceeds the threshold at 84, a determination is made whether that output from the scattered reflection sensor has a low frequency at 134. If such an output has a low frequency, the controller 26 determines that no wiper activation is required at 86. An example scenario in which these conditions may exist includes the output from a scattered reflection sensor being based on a reflection from one of the windshield wipers 24 as it was moving across the windshield 22.

If the determination made at 134 indicates that the frequency is not low enough to be ignored, a determination is made at 136 whether the frequency of the output from the scattered reflection sensor is high. If so, the controller 26 determines that a condition of the windshield 22 includes debris or a substance on the windshield 22. Under this condition, the controller 26 activates the windshield wiper assembly to include applying a washing fluid to the windshield 22 at 138. In one example, under this condition, the controller 26 resets all counters used for tracing the outputs from the sensors of the device 30.

As can be appreciated from the approach summarized in FIG. 5, the control approach includes the controller 26 determining if the first magnitude from the first output exceeds at least one predetermined magnitude threshold and determines if the first frequency exceeds at least one frequency threshold. Further, the processor of the controller 26 is configured to determine the condition of the windshield as a first condition that includes a first level of precipitation when the first magnitude exceeds a first magnitude threshold, such as the threshold LT, and the second output from a scattered reflection sensor does not indicate any radiation incident on a scattered reflection sensor. The processor of the controller 26 is also configured to determine that the condition of the windshield 22 is a second condition that includes a second level of precipitation that is greater than the first level of precipitation when the first magnitude exceeds a second magnitude threshold, such as the threshold MT, that is higher than the first magnitude threshold and the second output from a scattered reflection sensor indicates radiation incident on the scattered reflection sensor. The processor of the controller 26 is also configured in this example to determine a condition of the windshield as a third condition that includes a third level of precipitation that is greater than the second level of precipitation when the first magnitude exceeds a third magnitude threshold, such as the threshold HT, that is greater than the second magnitude threshold and the second output from at least one of the scattered reflection sensors indicates radiation incident on the scattered reflection sensor with a high frequency of incidence.

As demonstrated in the flowchart of FIG. 5, the processor of the controller 26 is also configured to control the windshield wiper assembly based on the determined condition of the windshield. In the illustrated example, the controller 26 causes the windshield wiper assembly to swipe the windshield once based on determining that the condition of the windshield is the first condition mentioned above. The controller 26 causes the windshield wiper assembly to operate at a selected speed, such as a low, medium or high speed, based on the frequency of the first output from the internal reflection sensor and a frequency of incidence of radiation detected by a scattered reflection sensor when the condition of the windshield is the second condition mentioned above. The processor of the controller 26 is also configured to cause the windshield wiper assembly to operate at a high speed when the condition of the windshield corresponds to the third condition mentioned above.

In an example embodiment, the memory associated with the processor of the controller 26 includes instructions that cause the controller 26 to operate according to the process shown in FIG. 5, for example. The memory associated with the processor of the controller 26 may also be used for at least temporarily storing sensor output values that allow the processor to make the determinations resulting in the type of control summarized in FIG. 5.

The various thresholds, amounts of precipitation and speeds of wiper operation may be chosen to meet the needs of a particular vehicle or wiper system. Those skilled in the art who have the benefit of this description will be able to select appropriate values for such parameters.

A rain or substance detecting device and method designed according to an embodiment of this invention, like that shown in the figures and described above, allows for a more robust detection system that is capable of detecting the presence of rain on a windshield, other substances on a windshield, and raindrops approaching a windshield. Embodiments of this invention allow for realizing such operation while providing cost and space savings compared to other detectors, in part, because there is no requirement for any collimating lenses or prisms to direct radiation at the windshield. Additionally, the dual mode operation results in enhanced detection performance compared to the performance available from previous detector configurations.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

We claim:

1. A device for detecting rain or a substance on a windshield, the device comprising:
    at least one radiation source that emits radiation toward a detection area on the windshield in a direction such that a first portion of the radiation reflects from the windshield and a second portion of the radiation passes through the windshield;
    an internal reflection sensor situated relative to the at least one radiation source such that at least some of the first portion of the radiation that reflects from the detection area on the windshield is incident on the internal reflection sensor, the internal reflection sensor providing a first output that is indicative of an amount of the first portion of the radiation that is incident on the internal reflection sensor, the first output having a characteristic that differs based on whether at least one rain drop is on the windshield in the detection area;
    a scattered reflection sensor situated relative to the at least one radiation source differently than the internal reflection sensor such that at least some of the second portion of the radiation reflecting from rain near the windshield or a substance on the windshield may be incident on the scattered reflection sensor, the scattered reflection sensor providing a second output indicative of an amount of radiation incident on the scattered reflection sensor; and
    a processor that is configured to determine a condition of the windshield based on the first output and the second output.

2. The device of claim 1, wherein the radiation source emits light.

3. The device of claim 2, wherein the radiation source comprises a laser diode.

4. The device of claim 3, wherein the radiation source comprises a near infrared laser diode.

5. The device of claim 1, wherein the characteristic of the first output includes a first magnitude and a first frequency.

6. The device of claim 5, wherein the processor is configured to
determine if the first magnitude exceeds at least one predetermined magnitude threshold; and
determine if the first frequency exceeds at least one frequency threshold.

7. The device of claim 6, wherein the processor is configured to
determine that the condition of the windshield is a first condition that includes a first level of precipitation when the first magnitude exceeds a first magnitude threshold and the second output does not indicate any radiation incident on the scattered reflection sensor;
determine that the condition of the windshield is a second condition that includes a second level of precipitation that is greater than the first level of precipitation when the first magnitude exceeds a second magnitude threshold that is higher than the first magnitude threshold and the second output indicates radiation incident on the scattered reflection sensor; and
determine that the condition of the windshield is a third condition that includes a third level of precipitation that is greater than the second level of precipitation when the first magnitude exceeds a third magnitude threshold that is greater than the second magnitude threshold and the second output indicates radiation incident on the scattered reflection sensor with a high frequency of incidence.

8. The device of claim 7, wherein the processor is configured to
control a windshield wiper assembly based on the determined condition of the windshield;
cause the windshield wiper assembly to swipe the windshield once based on determining that the condition of the windshield is the first condition;
cause the windshield wiper assembly to operate at one of a low, medium or high speed based on the first frequency and a frequency of incidence of radiation incident on the scattered reflection sensor when the condition of the windshield is the second condition; and
cause the windshield wiper assembly to operate at a high speed when the condition of the windshield is the third condition.

9. The device of claim 6, wherein the processor is configured to
determine that a substance is on the windshield when the first output does not indicate any rain on the detection area and the second output indicates that radiation is incident on the scattered reflection sensor at a high frequency of incidence; and
cause a windshield wiper assembly to apply a windshield cleaner fluid to the windshield.

10. The device of claim 1, comprising:
at least one transreflective component between the radiation source and the windshield, the transreflective component allows the first portion of the radiation to pass through the transreflective component toward the detection area on the windshield and reflect a third portion of the radiation toward a second detection area on the windshield; and
a second internal reflection sensor situated relative to the at least one radiation source such that at least some of the third portion of the radiation that reflects from the second detection area on the windshield is incident on the second internal reflection sensor, the second internal reflection sensor providing a third output that is indicative of an amount of the third portion of the radiation that is incident on the second internal reflection sensor, the third output having a characteristic that differs based on whether at least one rain drop is on the windshield in the second detection area.

11. The device of claim 10, wherein
the first portion of the radiation is directed at the detection area on the windshield at an angle that results in the first portion of the radiation reflecting from the detection area toward the internal reflection sensor; and
the third portion of the radiation is directed at the second detection area on the windshield at an angle that results in the second portion of the radiation reflecting from the second detection area toward the second internal reflection sensor.

12. The device of claim 1, wherein
the first portion of the radiation is directed at the detection area on the windshield at an angle that results in the first portion of the radiation reflecting from the detection area toward the internal reflection sensor; and
the characteristic of the first output includes a first magnitude that decreases in an amount corresponding to an amount of rain on the detection area.

13. A method of detecting rain or a substance on a windshield, the method comprising:
emitting radiation toward a detection area on the windshield in a direction such that a first portion of the radiation reflects from the windshield and a second portion of the radiation passes through the windshield;
using an internal reflection sensor for detecting at least some of the first portion of the radiation that reflects from the detection area on the windshield that is incident on the internal reflection sensor;
generating a first output from the internal reflection sensor that is indicative of an amount of the first portion of the radiation that is incident on the internal reflection sensor, the first output having a characteristic that differs based on whether at least one rain drop is on the windshield in the detection area;
using a scattered reflection sensor for detecting at least some of the second portion of the radiation reflecting from rain near the windshield or a substance on the windshield;
generating a second output from the scattered reflection sensor indicative of an amount of radiation incident on the scattered reflection sensor; and
determining a condition of the windshield based on the first output and the second output.

14. The method of claim 13, wherein the radiation comprises light.

15. The method of claim 13, wherein the characteristic of the first output includes a first magnitude and a first frequency.

16. The method of claim 15, comprising
determining if the first magnitude exceeds at least one predetermined magnitude threshold; and
determining if the first frequency exceeds at least one frequency threshold.

17. The method of claim 16, comprising:
determining that the condition of the windshield is a first condition that includes a first level of precipitation when the first magnitude exceeds a first magnitude threshold and the second output does not indicate any radiation incident on the scattered reflection sensor;

determining that the condition of the windshield is a second condition that includes a second level of precipitation that is greater than the first level of precipitation when the first magnitude exceeds a second magnitude threshold that is higher than the first magnitude threshold and the second output indicates radiation incident on the scattered reflection sensor; and determining that the condition of the windshield is a third condition that includes a third level of precipitation that is greater than the second level of precipitation when the first magnitude exceeds a third magnitude threshold that is greater than the second magnitude threshold and the second output indicates radiation incident on the scattered reflection sensor with a high frequency of incidence.

18. The method of claim 17, comprising controlling a windshield wiper assembly based on the determined condition of the windshield including:

causing the windshield wiper assembly to swipe the windshield once based on determining that the condition of the windshield is the first condition;

causing the windshield wiper assembly to operate at one of a low, medium or high speed based on the first frequency and a frequency of incidence of radiation incident on the scattered reflection sensor when the condition of the windshield is the second condition; and causing the windshield wiper assembly to operate at a high speed when the condition of the windshield is the third condition.

19. The method of claim 16, comprising determining that a substance is on the windshield when the first output does not indicate any rain on the detection area and the second output indicates that radiation is incident on the scattered reflection sensor at a high frequency of incidence; and causing a windshield wiper assembly to apply a windshield cleaner fluid to the windshield.

20. The method of claim 13, comprising:

directing a third portion of the radiation toward a second detection area on the windshield;

using a second internal reflection sensor for detecting at least some of the third portion of the radiation that reflects from the second detection area on the windshield; and generating a third output from the second internal reflection sensor that is indicative of an amount of the third portion of the radiation that is incident on the second internal reflection sensor, the third output having a characteristic that differs based on whether at least one rain drop is on the windshield in the second detection area.

* * * * *